(12) United States Patent
Bruggemann et al.

(10) Patent No.: US 9,610,407 B2
(45) Date of Patent: Apr. 4, 2017

(54) MEDICAMENT DELIVERY DEVICES

(71) Applicant: SANOFI-AVENTIS DEUTSCHLAND GMBH, Frankfurt am Main (DE)

(72) Inventors: Ulrich Bruggemann, Frankfurt am Main (DE); Christopher Langley, Warwickshire (GB); Christopher Jones, Worcestershire (GB); Scott Preece, Coventry (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/793,076

(22) Filed: Jul. 7, 2015

(65) Prior Publication Data

US 2015/0306316 A1     Oct. 29, 2015

Related U.S. Application Data

(63) Continuation of application No. 13/145,835, filed as application No. PCT/EP2010/051272 on Feb. 3, 2010, now Pat. No. 9,107,996.

(30) Foreign Application Priority Data

Feb. 5, 2009   (EP) ..................................... 09001576

(51) Int. Cl.
*A61M 5/20* (2006.01)
*A61M 5/145* (2006.01)
*A61M 5/315* (2006.01)

(52) U.S. Cl.
CPC .......... *A61M 5/20* (2013.01); *A61M 5/14546* (2013.01); *A61M 5/31565* (2013.01);
(Continued)

(58) Field of Classification Search
CPC ................ A61M 5/20; A61M 5/31565; A61M 5/14546; A61M 2205/3327
See application file for complete search history.

(56) References Cited

U.S. PATENT DOCUMENTS 5,437,635 A    8/1995  Fields et al.
5,989,221 A    11/1999 Hjertman
(Continued)

FOREIGN PATENT DOCUMENTS

EP    2014323    1/2009
WO    98/00188   1/1998
(Continued)

OTHER PUBLICATIONS

International Search Report for Int. App. No. PCT/EP2010/051272, mailed Jul. 12, 2010.

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A medicament delivery device comprises a housing, a holder within the housing for receiving a medicament cartridge, a piston rod for driving a bung of the medicament cartridge, a drive mechanism including a motor for providing an output drive to the piston rod for delivering the medicament and control means for controlling operation of the device. The device is additionally provided with a bung sensor for sensing when the piston rod is in contact with the bung and the control means is operative for advancing the drive of the piston rod towards the bung.

14 Claims, 2 Drawing Sheets

(52) U.S. Cl.
    CPC ..... *A61M 5/14566* (2013.01); *A61M 5/31546* (2013.01); *A61M 2005/31588* (2013.01); *A61M 2205/14* (2013.01); *A61M 2205/3327* (2013.01)

(56) References Cited

U.S. PATENT DOCUMENTS

| | | |
|---|---|---|
| 6,979,309 B2 | 12/2005 | Burbank et al. |
| 7,347,836 B2 * | 3/2008 | Peterson ........... A61M 5/14228 604/31 |
| 7,704,231 B2 * | 4/2010 | Pongpairochana ..... A61M 5/20 604/131 |
| 2011/0160655 A1 | 6/2011 | Hanson et al. |

FOREIGN PATENT DOCUMENTS

| | | |
|---|---|---|
| WO | 99/65548 | 12/1999 |
| WO | 01/83005 | 11/2001 |
| WO | 03/099357 | 12/2003 |
| WO | 2005/002652 | 1/2005 |

* cited by examiner

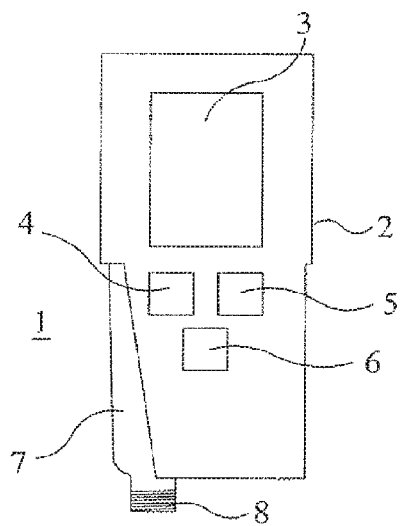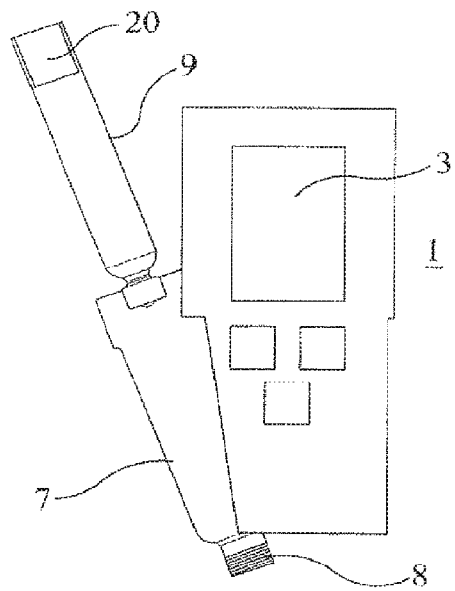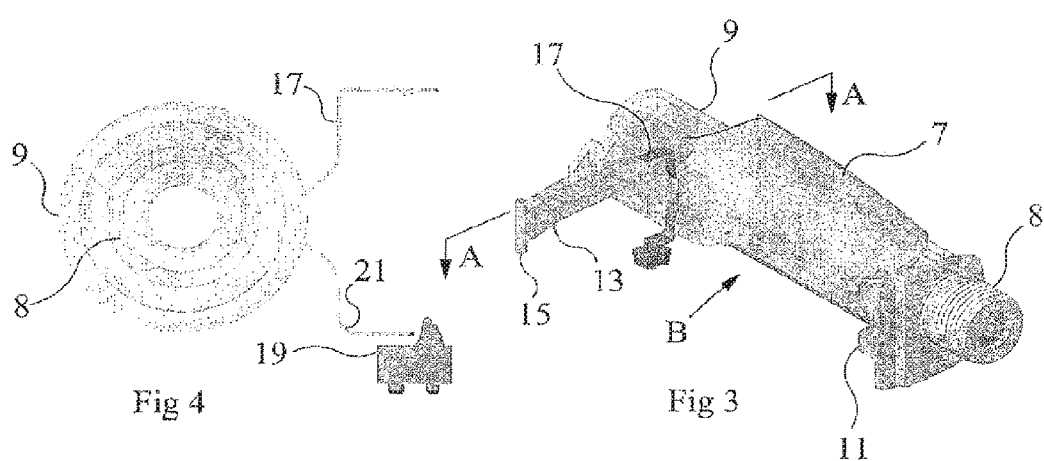

MEDICAMENT DELIVERY DEVICES

CROSS REFERENCE TO RELATED APPLICATIONS

The present application is a continuation of U.S. patent application Ser. No. 13/145,835, filed Dec. 6, 2011, which is a U.S. National Phase Application pursuant to 35 U.S.C. §371 of International Application No. PCT/EP2010/051272 filed Feb. 3, 2010, which claims priority to EP Patent Application No. 09001576.9 filed on Feb. 5, 2009. The entire disclosure contents of these applications are herewith incorporated by reference into the present application.

FIELD OF INVENTION

This invention relates to medicament delivery devices for delivering medicine to the human or animal body and in particular to electronically controlled auto-injectors having a replaceable medicament cartridge. Such devices are commonly used by those with diabetes for the administration of insulin.

BACKGROUND

Medicament delivery devices are routinely used by persons without formal medical training, i.e. patients where self-management of their condition is increasingly common. These circumstances set a number of requirements for medicament delivery devices of this kind The injector should be robust in construction, yet easy to use in terms of its operation by a user and the manipulation of the parts. In the case of those with diabetes, many users will be of impaired vision and may also be physically infirm. Devices that are too large or cumbersome may therefore prove difficult to use, particularly someone with reduced dexterity.

U.S. Pat. No. 5,989,221 describes an electronically controlled injection device in which the readying of the device for administering and the subsequent drug delivery therefrom is controlled by an electronic control unit. Specifically, the control unit comprises a position or attitude sensor for transmitting a signal so that the readying of the device cannot take place unless the longitudinal axis of the injection cartridge is in a predetermined direction. This is in the context of removing air or mixing drug components. The control unit is also operative for driving a piston rod a predetermined distance for delivery of a drug dose.

In such prior art devices, the user is still required to prime the device after installation of the medicament cartridge. Moreover, such devices may under dose particularly in cases where the medicament cartridge is not properly seated within the device after insertion by the user.

SUMMARY

It is an aim of the present invention to provide a medication delivery device where replacement of the medicament cartridge is easier to carry out by the user.

According to the present invention, there is provided a medicament delivery device for delivering a medicament to a patient, wherein the medicament delivery device comprises: a housing; a holder within the housing for receiving a medicament cartridge; a piston rod for driving a bung of the medicament cartridge; a drive mechanism including a motor for providing an output drive to the piston rod for delivering the medicament; and control means for controlling operation of the device; characterised in that:

a bung sensor is provided for sensing when the piston rod is in contact with the bung;
wherein the control means is operative for advancing drive of the piston rod towards the bung.

In a preferred embodiment, the control means is operative for advancing the drive of the piston rod until the bung sensor senses that the piston rod is in contact with the bung. A latch sensor may be provided for sensing the position of the holder as the holder moves from an open position to a closed position. In this case, the control means is operative for advancing the drive of the piston rod only when the latch sensor senses the holder is in the closed position.

Furthermore, a cartridge sensor may be provided for sensing the presence of a medicament cartridge in the holder. In this embodiment, the control means is operative for advancing the drive of the piston rod when the cartridge sensor senses the presence of the medicament cartridge and the latch sensor senses that the holder is in a closed position.

The control means is operative to stop further advancement of the piston rod: a) when the bung sensor senses that the piston rod is in contact with the bung; or b) when the cartridge has moved to a seated position within the housing after initial contact between the piston rod and the bung. In this case, the force needed to actuate the bung sensor is greater than the sliding friction between the cartridge and the holder. The holder may include a door of the medicament delivery device. The control means may be operative for advancing the piston rod drive when the cartridge sensor senses that the medicament cartridge is in a predetermined (i.e. 'correct' or 'seated') position relative to the holder to deliver a dose of medicament.

In an alternative embodiment, the latch sensor and the bung sensor may each generate sensor signals that are combined so that the combined signal sent to the control means indicates that the cartridge is present and/or in the correct position when the piston rod contacts the cartridge bung.

In another embodiment, the control means is operative to backwind the piston rod by a predetermined amount when the bung sensor senses that the piston rod is in contact with the bung. This is advantageous in the case where the bung sensor is in the form of a dome switch or other pressure switch (including solid state switches and pressure switches), thus leaving the dome switch in an open position. For dosing, the control means drives the piston rod by an amount that compensates for this backwind.

Any one or all of the cartridge, latch and bung sensors may be switches that signal their respective sensing function to the control means.

Embodiments of the present invention are advantageous in that the medicament delivery device automatically advances the piston rod towards the cartridge bung when a cartridge is present and the door/holder of the injector is closed. This simplifies the number of operations for the user, including avoiding a need for the user to dial an air-shot dose to position the piston rod against the bung. Battery life is saved by avoiding drive of the piston rod when no cartridge is present. As the cartridge is properly or fully seated within the holder, a further advantage is that the likelihood of under-dosing following insertion of a new or used cartridge is reduced.

The term "medicament delivery device" according to instant invention shall mean a single-dose or multi-dose or pre-set dose or pre-defined, disposable or re-useable device designed to dispense a user selectable or pre-defined dose of a medicinal product, preferably multiple doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "medicament delivery device" may refer to a needle-based device providing multiple doses having an electrical drive mechanism, which is designed for use by persons without formal medical training such as patients. Preferably, the drug delivery device is of the automated-type, i.e. an auto-injector.

The term "housing" according to instant invention shall preferably mean any exterior housing ("main housing", "body", "shell") or interior housing ("insert", "inner body") having a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

The term "motor" according to the instant invention shall preferably mean any motorised means for driving the gearing system and ultimately the input drive means. In the instant invention a stepper motor is preferably utilised although any means for driving the gearing system or the drive means, including a mechanical or manual actuation means, may also be incorporated into the device.

The "proximal end" of the device or a component of the device shall mean the end, which is furthest away from the dispensing end of the device.

The "distal end" of the device or a component of the device shall mean the end, which is closest to the dispensing end of the device.

Devices embodying the invention may be usefully deployed in re-useable medicament delivery devices that comprise replaceable medicament cartridges and may also be deployed within an auto-injector device.

BRIEF DESCRIPTION OF THE FIGURES

The invention will now be further described by way of example with reference to the accompanying drawings, in which like reference numerals designate like elements:

FIG. 1 is a front view of a medicament delivery device that may include an embodiment of the present invention;

FIG. 2 is a front view of the medicament delivery device of FIG. 1 with a medicament cartridge door shown in an open position for receiving a medicament cartridge;

FIG. 3 is a perspective view of a cartridge sensor/switch;

FIG. 4 is a sectional view taken along line A-A of FIG. 3;

DETAILED DESCRIPTION

Figure 5:
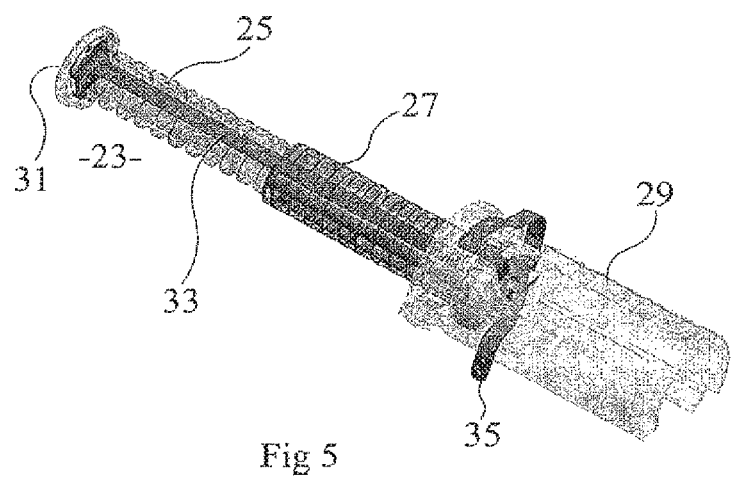
FIG. 5 is a perspective view of a bung sensor/switch.

In FIG. 1, a medicament delivery device 1 comprises a case 2 having a display 3 for displaying functional information relating to the operation of the medicament delivery device, including the set dose, number of doses remaining in the medicament cartridge. User interface buttons 4, 5 and 6 are provided to allow the user to operate the injector including priming, setting a dose, opening a medicament cartridge holder and door 7, and activating the dispensing of the set dose. A threaded needle attachment 8 is provided to which a needle can be attached for dose delivery and subsequently removed and discarded. A cover (not shown) may be provided to fit over the lower portion of the case 2 to assist in protect the device from the ingress of particles and fluid. FIG. 2 shows the medicament delivery device 1 with the cartridge holder and door 7 in an open position for receiving a replacement medicament cartridge 9.

Figure 6:
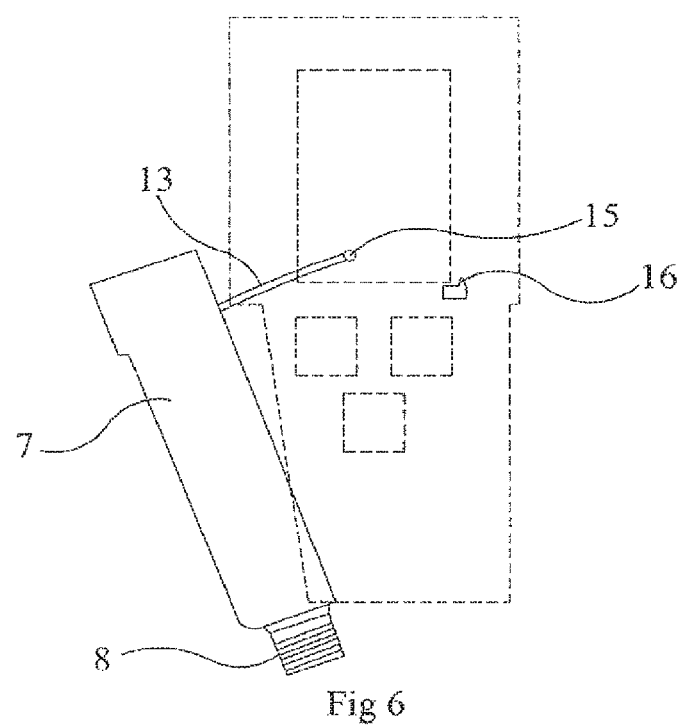
FIG. 6 is a transparent view of the medicament delivery device of FIG. 2 to show the door or holder sensor/switch.

FIG. 3 shows the cartridge holder and door 7 in more detail, with the cartridge 9 seated therein. The holder 7 is pivotally fixed to the case 2 by an attachment 11 so that the holder 7 can move between an open position (see FIG. 2) and a closed position (see FIG. 1). An arm 13 extends into the case 2 and has a stop 15 to limit the outward extent of the door/holder 7 in the direction of arrow B. The stop 15 may also engage a latch switch or sensor 16, as shown in FIG. 6, which is provided for sensing when the holder 7 moves from an open or a closed position. An actuator/lever 17 is provided for sensing the presence of the cartridge 9 and closure of the holder 7 within the case 2. FIG. 4 is a sectional view taken along line A-A of FIG. 3 and shows the cartridge 9 and the actuator/lever 17. In this embodiment, the lever 17 forms part of a contact switch 19 that has a displaceable contact 21. This displaceable contact 21 is moved to change the state of the switch 19 when the cartridge is received in the holder 7. The lever 17, contact switch 19 and displaceable contact 21 together form a cartridge sensor.

FIG. 5 is a perspective view of a telescopic piston rod assembly 23 that comprises slidable components 25 and 27 which telescope within a housing 29. The assembly 23 is provided with a dome switch 31 at the end thereof that contacts a bung 20 of the cartridge 9. The dome switch 31 is connected to a flexible PCB element 33 that extends within the components 25 and 27. The element 33 emerges from the other end thereof, through the housing 29 to terminate at a contact 35. The contact 35 is coupled to a control means (not shown) that is operative for controlling the device, including the drive of the piston rod.

FIG. 6 is a transparent view of the medicament delivery device of FIG. 2 and shows the approximate location of the latch switch or sensor 16 and the stop 15 within the device. Although shown as a contact switch, it may be appreciated that the latch switch or sensor may alternatively be a mechanical latch or any other switch or sensor known in the art.

The operation of the medicament delivery device 1 is as follows. The latch sensor 16 is provided for sensing when the holder 7 moves from an open or closed position and the bung sensor 31 is operative for sensing when the piston rod 25, 27 is in contact with the bung 20. The control means is operative for advancing drive of the piston rod 25, 27 towards the bung 20 provided that the latch sensor 16 senses that the holder 7 has moved to a closed position. The control means is operative for advancing the drive of the piston rod 25, 27 until the bung sensor 31 senses that the piston rod is in contact with the bung 20.

A cartridge sensor 17, 19, 21 is provided for sensing the presence of a medicament cartridge 9 in the holder 7. In this case, the control means is operative for advancing the drive of the piston rod 25, 27 when the cartridge sensor 17, 19, 21 senses the presence of the medicament cartridge and the latch sensor 16 senses that the holder 7 has moved from an open position to a closed position.

It may also be beneficial for the cartridge sensor 17, 19, 21 to only be operative after the latch sensor 16 detects whether the holder 7 has been opened or closed. While the holder is not in a closed position, it is not necessary to monitor the cartridge sensor. This may increase battery life of the device.

In this case, in order to load a medicament cartridge 9 into the device 1, the holder 7 (without a cartridge) may be opened to the position shown in FIG. 2. The movement of the holder 7 from the closed position to the open position is detected by the latch sensor 16. The signal from the latch sensor 16 prompts the control means to watch the cartridge sensor 17, 19, 21 to determine if a medicament cartridge 9 is present. In the present case, no cartridge is present, so no signal is detected. Therefore, the control means does not advance the drive of the piston rod 25, 27. This also aids battery life.

A medicament cartridge 9 may then be placed into the holder 7 and the holder closed. As the holder 7 closes, the latch switch 16 detects the movement of the holder, prompting the control means to watch the cartridge sensor 17, 19, 21. As a medicament cartridge 9 is present within the holder 7 and the holder is closed, the displaceable contact 21 is in contact with the switch 19, indicating the presence of a medicament cartridge. As both the latch sensor 16 and the cartridge sensor 17, 19, 21 have sensed that the holder 7 is closed and the medicament cartridge 9 is present, the control means is operative for advancing the drive of the piston rod 25, 27.

The control means is operative to stop further advancement of the piston rod 25, 27: a) when the bung sensor 31 senses that the piston rod is in contact with the bung 20; or b) when the cartridge 9 has moved to a seated position within the holder (see FIG. 3) after initial contact between the piston rod and the bung. In this case, the force needed to actuate the bung sensor 31 is greater than the sliding friction between the cartridge 9 and the holder 7. The holder 7 may include a door of the medicament delivery device 1. The control means may be operative for advancing the piston rod drive when the cartridge sensor 17, 19, 21 senses that the medicament cartridge 9 is in a predetermined (i.e. 'correct' or 'seated') position relative to the holder to deliver a dose of medicament.

In an alternative embodiment, the latch sensor 16 and the bung sensor 31 may each generate sensor signals that are combined so that the combined signal sent to the control means indicates that the medicament cartridge 9 or holder 7 is present and/or in the correct position when the piston rod 25, 27 contacts the cartridge bung 20.

As the bung sensor 31 is in the form of a dome switch, the control means is operative to backwind the piston rod 25, 27 by a predetermined amount when the bung sensor 31 senses that the piston rod is in contact with the bung 20.

The invention claimed is:

1. A medicament delivery device for delivering a medicament to a patient, wherein the medicament delivery device comprises:
    a housing;
    a cartridge holder configured to accept a medicament cartridge, where the cartridge holder pivots with respect to the housing from an open position to a closed position and is not detachable from the housing;
    a telescoping piston rod having a distal end on one of at least two slidable parts that telescope relative to the housing to drive a bung of the medicament cartridge in a medicament delivery direction;
    a drive mechanism to move the distal end of the piston rod in both the medicament delivery direction and an opposite backwinding direction;
    a bung sensor provided at the distal end of the piston rod that senses when the piston rod is in contact with the bung;
    an arm connected to the cartridge holder that limits the pivoting motion of the cartridge holder relative to the housing through engagement of a stop on the arm in the open position; and
    a latch sensor that provides a signal that the cartridge holder is in the open position when the stop engages the latch sensor;
    wherein the drive mechanism will not move the piston rod when the cartridge holder is in the open position.

2. The medicament delivery device according to claim 1 where the latch sensor senses the position of the holder as the holder moves from an open position to a closed position or a closed position to an open position.

3. The medicament delivery device according to claim 1, comprising a cartridge sensor for sensing the presence of a medicament cartridge in the holder.

4. The medicament delivery device according to claim 1, wherein the drive mechanism advances the piston rod when the cartridge sensor senses the presence of the medicament cartridge and the latch sensor senses that the holder is in a closed position.

5. The medicament delivery device according to claim 1, wherein the drive mechanism stops further advancement of the piston rod: a) when the bung sensor senses that the piston rod is in contact with the bung; or b) when the cartridge has moved to a seated position within the housing after initial contact between the piston rod and the bung.

6. The medicament delivery device according to claim 1, wherein the latch sensor and the bung sensor each generate sensor signals that are combined to provide a combined signal that indicates that the cartridge is present and/or in the correct position when the piston rod contacts the cartridge bung.

7. The medicament delivery device according to claim 1, wherein the at least two slidable parts of the piston rod comprise a first component and a second component, the first component is slidable relative to the housing, the second component is slidable relative to the housing, and the first component and the second component are slidable relative to each other.

8. The medicament delivery device according to claim 1, wherein the open position is a most outward position of the cartridge holder relative to the housing.

9. The medicament delivery device according to claim 1, wherein the bung sensor is configured to be actuated only by a force that is greater than a sliding friction force between the medicament cartridge and holder.

10. An auto-injector including a medicament delivery device according to claim 1.

11. A method of operating a medicament delivery device comprising,
    opening a cartridge holder in a delivery device housing by pivoting the cartridge holder relative to the housing, where the cartridge holder is not detachable from the housing;
    activating a latch sensor in the housing to generate an open signal when a stop located on the cartridge holder engages the latch sensor;

inserting a medicament cartridge having a bung into the cartridge holder so that the medicament cartridge contacts a cartridge sensor to generate a cartridge signal;

closing the cartridge holder and disengaging the stop from the latch sensor to generate a closed signal;

advancing a piston rod having a distal end in a medicament delivery direction after generation of both the cartridge signal and the closed signal; and stopping the advance of the piston rod when a bung sensor on the distal end of the piston rod contacts the bung.

12. The method according to claim 11, wherein advancing the piston rod and stopping the advance of the piston rod are automatically performed by a control means of the medicament delivery device.

13. The method according to claim 12, wherein advancing the piston rod and stopping the advance of the piston rod are further performed by a stepper motor.

14. The method according to claim 11, wherein advancing the piston rod and stopping the advance of the piston rod are performed by a manually actuated drive mechanism.

\* \* \* \* \*